United States Patent [19]

Schwartz

[11] Patent Number: 6,038,476
[45] Date of Patent: Mar. 14, 2000

[54] SYSTEM AND METHOD FOR ANALYZING THE EFFICACY OF CARDIAC STIMULATION THERAPY

[75] Inventor: Allan R. Schwartz, Moorpark, Calif.

[73] Assignee: Pacesetter, Inc., Sylmar, Calif.

[21] Appl. No.: 09/096,590

[22] Filed: Jun. 12, 1998

[51] Int. Cl.[7] ................................................. A61N 1/37
[52] U.S. Cl. ................................................. 607/27; 607/4
[58] Field of Search ............................ 607/4, 5, 14, 15, 607/25, 32, 27

[56] References Cited

U.S. PATENT DOCUMENTS

| 5,012,814 | 5/1991 | Mills et al. . | |
| 5,052,399 | 10/1991 | Olive et al. . | |
| 5,088,488 | 2/1992 | Markowitz et al. . | |
| 5,306,293 | 4/1994 | Zacouto . | |
| 5,312,443 | 5/1994 | Adams . | |
| 5,330,505 | 7/1994 | Cohen . | |
| 5,413,594 | 5/1995 | Williams | 607/32 |
| 5,458,116 | 10/1995 | Egler . | |
| 5,458,620 | 10/1995 | Adams et al. . | |
| 5,513,645 | 5/1996 | Jacobson et al. . | |
| 5,522,850 | 6/1996 | Yomtov et al. . | |
| 5,755,736 | 5/1998 | Gillberg et al. | 607/4 |
| 5,824,014 | 10/1998 | Thong et al. | 607/4 |
| 5,836,971 | 11/1998 | Starkweather . | |
| 5,873,897 | 2/1999 | Armstrong et al. . | |
| 5,882,352 | 3/1999 | Duncan et al. | 607/4 |
| 5,891,170 | 4/1999 | Nitzsche et al. | 607/4 |

FOREIGN PATENT DOCUMENTS

| 2649506 | 10/1976 | Germany . |
| 228169 | 10/1985 | Germany . |

Primary Examiner—William E. Kamm
Assistant Examiner—Carl M. Layno

[57] ABSTRACT

An implantable stimulation device (ISD) for recording and displaying cardiac episode history for analyzing efficacy of cardiac therapy. The ISD applies anti-bradycardia therapy in patients who suffer from a slow heart rate, and antitachycardia therapy in patients who experience episodes of high heart rate and/or fibrillation. The ISD detects the occurrence of these episodes, applies the necessary therapy, and stores the chronology of these events in a special memory unit. An external device may be employed to telemetrically retrieve the stored data from the ISD memory unit, and display the data in a time-line fashion for analysis by a physician. The recordation of such data provides a valuable tool for the physician to track cardiac episode history and recommend the appropriate therapy for the patient.

27 Claims, 6 Drawing Sheets

SYSTEM AND METHOD FOR ANALYZING THE EFFICACY OF CARDIAC STIMULATION THERAPY

FIELD OF THE INVENTION

The invention relates generally to implantable devices such as cardiac pacemakers. More particularly, this invention relates to implantable devices, which record patient data for subsequent retrieval and display by an external device.

BACKGROUND OF THE INVENTION

When a patient is diagnosed with an abnormal cardiac rhythm, one form of therapy often applied is the use of an implantable medical device to restore normal rhythm to the heart. In case of a slow heart rate, a pacemaker is often used to deliver synchronized pulse stimuli to restore normal rhythm to the heart. If the heart rate is less than 60 beats per minute ("bpm"), the condition is known as bradycardia, and the delivery of the stimulation pulses is referred to as pacing. A variety of pacemakers are available to treat this condition by artificially stimulating myocardial tissues using electrical pulse stimuli. Conventional pacemakers known in the art typically include a built-in sensor circuit for sensing, through attached sensing electrodes, the rate at which the heart is beating. The fundamental way the pacemaker identifies the presence of a bradycardia is by detecting that the heart rate has reached below a critical value. Since most episodes of a bradycardia exhibit a rate less than 60 bpm, the pacemaker is typically programmed to apply therapeutic pacing pulses when this rate is reached.

In case of a fast heart rate, however, an Implantable Cardioverter-Defibrillator ("ICD") device is often used to deliver high energy stimulation pulse or pulses to restore normal rhythm to the heart. If the heart rate is greater than 150 bpm, the condition is known as tachycardia, and the delivery of the stimulation pulses is referred to as cardioversion. If the heart rate is greater than 240 bpm, then the condition is known as fibrillation. The condition is characterized by rapid and unsynchronized quivering of the atria or ventricles. If ventricular fibrillation ("VF") is involved, then the ICD device delivers higher energy stimulation pulses (referred to as "defibrillation") to recover the heart from its fibrillation state.

Conventional ICD devices known in the art typically include a built-in sensor circuit for sensing, through attached sensing electrodes, the rate at which the heart is beating. The fundamental way the ICD identifies the presence of a sustained ventricular tachycardia ("VT") is by detecting that the heart rate has exceeded a critical value. Since most episodes of sustained VT exhibit a rate in excess of 150 beats per minute ("bpm"), the ICD device is typically programmed to initiate a cardioversion therapy when this rate is reached. The type of therapy to be used depends on the device as well as the hemodynamic status of the patient during the tachyarrhythmia episode. For antitachycardia pacing, additional detection criteria may be programmed to enhance the certainty that a VT is present rather than a supraventricular tachyarrhythmia (e.g., atrial fibrillation). Such detection criteria are well known in the art and include the identification of cycle length stability, the abruptness of onset of the tachyarrhythmia, and the duration of a sustained rate. If the sensed heart rate is higher than a rate threshold of around 240 bpm, then a VF is often the sensed event. The ICD is then triggered to deliver a defibrillation pulse to the heart through the stimulating electrodes.

Typically, the physician who is implanting the pacemaker and/or ICD device determines the correct rate thresholds, which are needed for the particular patient. In programming the pacemaker/ICD device, however, the rate thresholds may not necessarily be appropriate for the particular patient. In addition, due to a coupled drug therapy, the patient therapeutic levels may often vary over time. When the patient is not being monitored, the physician will not be able to identify the effect of the selected therapy levels. Consequently, the physician cannot monitor the operation of the pacemaker/ICD device and, particularly, the patient's heart response to the applied therapy. Therefore, there is a need to enable a physician to better diagnose a patient's particular need for a cardiac therapy. The physician should determine a patient's progress in connection with and response to the applied therapy.

SUMMARY OF THE INVENTION

To overcome the disadvantages and limitations of the prior art, the invention provides a system and method for automatically recording diagnostic and therapeutic information from patients implanted with an ICD and/or pacemaker devices (hereinafter collectively referred to as an "implantable stimulation device," i.e., ISD). The recorded data are displayed in a timeline fashion to determine the efficacy of therapeutic application.

In one embodiment, the invention provides a system for analyzing efficacy of cardiac stimulation during a cardiac episode. The system comprises a first circuit sensing a patient's cardiac rhythm as a function of time, and a detector circuit detecting a pathological cardiac rhythm upon its occurrence. The system further comprises a processor classifying the pathological rhythm into one of a plurality of zones, and a second circuit applying a cardiac stimulation therapy to the patient's heart in response to the pathological cardiac rhythm. The system further comprises a memory storing data related to the pathological cardiac rhythm and stimulation therapy, and a display unit displaying the data for analysis.

Furthermore, in an implantable cardiac stimulation device, the invention provides a method of analyzing efficacy of cardiac stimulation therapy. The method comprises the steps of sensing a patient's cardiac rhythm as a function of time, and detecting a pathological cardiac rhythm upon occurrence. The method further comprises the steps of classifying the pathological rhythm into one of a plurality of zones, and applying a cardiac stimulation therapy to the patient's heart in response to the detected pathological cardiac rhythm. The method further comprises the steps of recording data related to the pathological cardiac rhythm and stimulation therapy, and displaying the data for analysis.

BRIEF DESCRIPTION OF THE DRAWINGS

The above and other aspects, features and advantages of the invention will be better understood by referring to the following detailed description, which should be read in conjunction with the accompanying drawings, in which.

DETAILED DESCRIPTION OF THE PREFERRED EMBODIMENT

One preferred embodiment of the invention is described in the following description. This description is not to be taken in a limiting sense but is made merely for the purpose of describing the general principles of the invention. The scope of the invention should be ascertained with reference to the appended claims.

The invention provides a system and method for recording diagnostic information from a patient with an implantable device such as a pacemaker and/or an implantable cardioverter-defibrillator (collectively referred to as "ISD"). The invention provides the ability to automatically record cardiac episode history in a time-line fashion for later display by an external device. The recorded information includes important data such as the date and time of the cardiac event, the nature of the cardiac event, the type of therapy applied by the implanted device, and the various heart rates during the cardiac episode. With this information, the physician is able to determine the efficacy of the applied therapy by analyzing the chronology of a cardiac episode from onset to termination.

Figure 1:
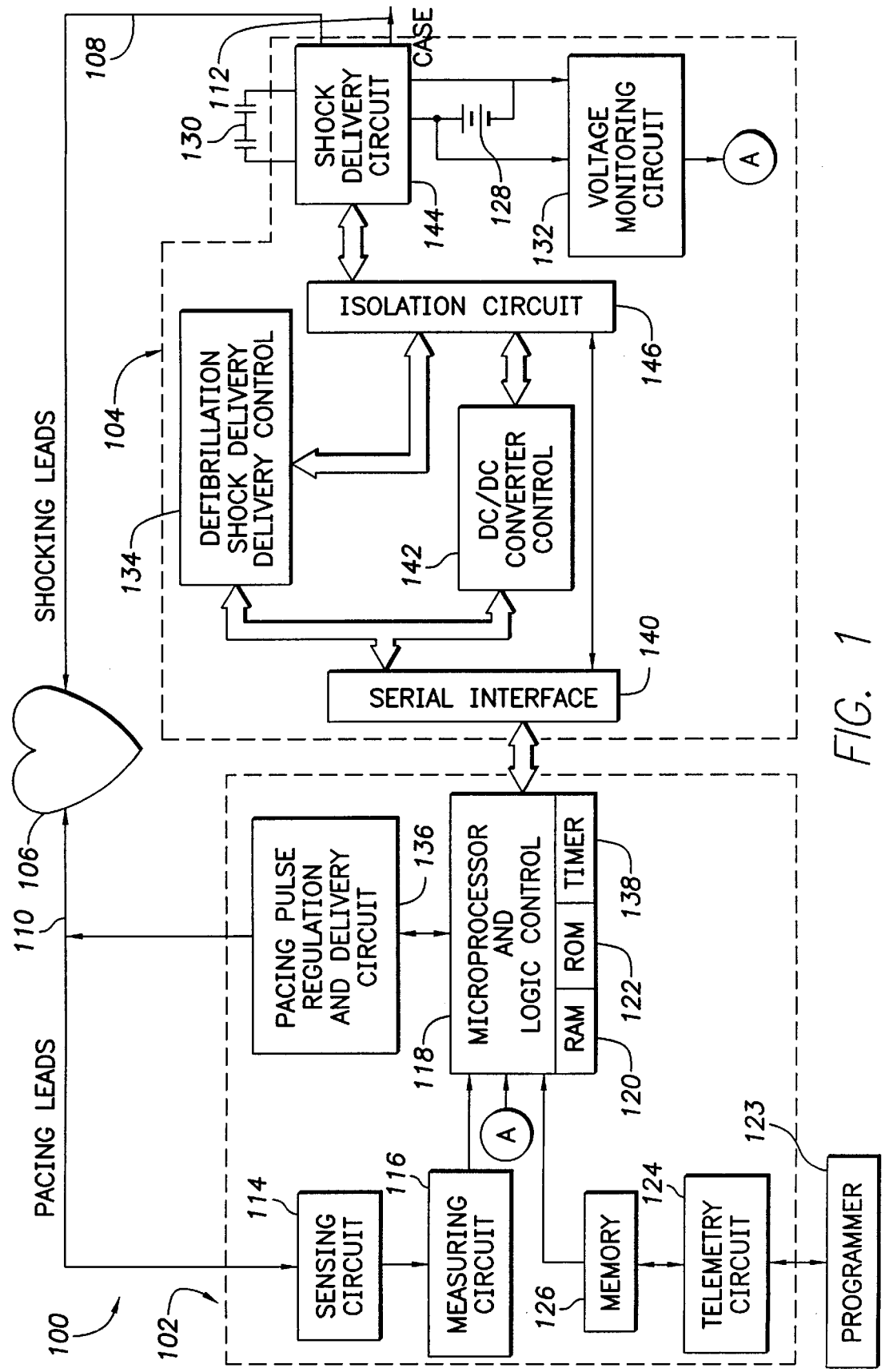
FIG. 1 is a functional block diagram of an exemplary implantable stimulation device employed in one embodiment of the invention.

FIG. 1 shows a functional block diagram of an exemplary pacemaker with the ICD device used in the invention. The implantable stimulation device (ISD) 100 includes a pacing module 102, which is responsible for regulation and delivery of pacing therapy as well as overall operational control of the ISD 100. The ISD 100 further includes a cardioversion module 104 to control, generate, and deliver cardioversion and defibrillation shocks to the heart 106.

The ISD 100 preferably administers therapeutic shocks (i.e., cardioversion or defibrillation shocks) or pacing pulses to a patient's heart 106 in order to interrupt cardiac arrhythmias or supply antitachycardia pacing, respectively. However, the invention also may be practiced with dedicated implantable cardioverters and defibrillators. The ISD 100 delivers the therapeutic cardioversion or defibrillation shocks to the patient's heart 106 through a plurality of shocking leads 108. Low energy pacing pulses are administered to the patient's heart 106 through a pacing lead system 110. The pacing lead system 110 also serves to sense intrinsic cardiac activity during periods when electrical stimulation is not being applied to the heart 106. Further, an electrically conductive enclosure 112 of the ISD 100 may be used as an electrode in the delivery of therapeutic shocks or pacing pulses.

The lead system 110 feeds physiological and electrophysiological data in the form of analog signals from the patient's heart 106 to a sensing circuit 114. The lead system 110 may also include sensors (not shown) which monitor cardiac mechanical activity. The sensing circuit 114 typically amplifies the incoming analog signals and filters out undesired noise signal components. The sensing circuit 114 sends these signals to a measuring circuit 116 where the signals are digitized and formatted for use by a microprocessor and logic control circuit 118 (the "microprocessor"). Then, the microprocessor 118 analyzes the digital signals to determine the existence of an arrhythmia.

The microprocessor 118 performs its analysis using programmable routines located in a memory device, e.g., RAM 120 or ROM 122. A variety of memory devices may be used with the invention. The RAM 120 or ROM 122 is preferred over an external discrete memory device (not shown) because of the savings in processing speed, power consumption and their effect on the overall size of the ISD 100. Communication with and programming of the ISD 100 is accomplished by a programmer 123 which communicates with the ISD 100 through a telemetry circuit 124. Telemetry data are transmitted to and from the microprocessor 118 through a memory 126.

Prior to the detection of an arrhythmia, the microprocessor 118 monitors the actual voltage of a battery 128—used to charge a pair of capacitors 130 as more fully described below—to forecast a minimum time-to-therapy. The microprocessor 118 further monitors other device parameters including capacitor discharge times, and possible programmable delays needed to properly synchronize a cardioversion shock with the ECG wave patterns. A voltage monitoring circuit 132 determines the actual voltage of the battery 128 and communicates this information to the microprocessor 118. If pacing pulses are needed, for example, to treat bradycardia, the microprocessor 118 enables a pacing pulse regulation and delivery circuit 136, which generates and transmits the pulses to the patient's heart 106 at appropriate times through the pacing lead system 110.

In response to a detected tachycardia, the microprocessor 118 starts the running of a timer 138 and, through a serial interface 140, instructs a DC/DC control circuit 142 to begin charging the pair of capacitors 130 in series with each other to their target voltage. The DC/DC control circuit 142, in turn, instructs a shock delivery circuit 144, through an isolation circuit 146, to begin charging the capacitors 130. The DC/DC control circuit 142 performs all control and logic operations needed by the shock delivery circuit 144 to create a high frequency AC voltage, which is rectified into a DC high voltage for application to the capacitors 130. The defibrillation shock delivery control circuit 134 performs all logic and control operations needed to deliver a desired therapeutic shock to the heart 106, including controlling the delivery, energy content, and waveform of a therapeutic shock.

In one embodiment, the isolation circuit 146 includes a transformer interface (not shown), which is used to electrically isolate the low voltage circuits of both the defibrillation shock delivery control circuit 134 and the DC/DC control circuit 142, as well as the pacing module 102, from exposure to high voltages. All control and feedback signals preferably pass through the isolation circuit 146 in order to prevent harm to the low voltage circuits of the ISD 100.

A high voltage charge is typically generated in the following manner: the battery 128 supplies a voltage typically on the order of 6.4 volts to the shock delivery circuit 144. When instructed to do so by the DC/DC control circuit 142, and preferably by employing a DC/DC converter, which may be of conventional design, the shock delivery circuit 144 produces a high frequency pulsed voltage substantially equal in magnitude to the voltage of the battery 128. The high frequency pulsed low voltage is converted to high frequency pulsed high voltage by a step-up transformer (not shown). This high frequency high voltage is then full-wave rectified by the shock delivery circuit 144. The rectified signal is applied to the capacitors 130. The capacitors 130 charge incrementally with each rectified pulse to a voltage corresponding to either the nominal or increased shock energy level depending upon which one is set to be delivered. The shock delivery circuit 144 informs the defibrillation shock delivery control circuit 134, through the isolation circuit 146, when the capacitors 130 are sufficiently charged (i.e., charged to their target voltage).

By analyzing the digitized signals provided by the measuring circuit 116, the microprocessor 118 ultimately determines the type of arrhythmia occurring. The microprocessor 118 categorizes the sensed signals into one of several rate zones. The rate zones are typically programmable as lower and upper limits by the physician. The rate zones are used to determine the kind of therapy to be applied to the heart 106. In this embodiment, there are at least five rate zones: (1) bradycardia having a heart rate of less than 60 bpm; (2) normal sinus rate ("NSR") having a heart rate between 60 and 100 bpm; (3) ventricular tachycardia 1 ("VT1") having a heart rate between 100 and 150 bpm; (4) ventricular tachycardia 2 ("VT2") having a heart rate between 150 and 230 bpm; and (5) ventricular fibrillation ("VF") having an unsynchronized heart rate greater than 230 bpm. The ISD 100 distinguishes among the various heart conditions, and delivers a particular type or pattern of high energy stimulation pulses specifically applicable to the detected heart condition.

The categorization of rate zone prescribes a predetermined range of shock energies to be delivered corresponding to the various therapeutic energy ranges for the occurring cardiac event. For example, if the microprocessor 118 determines that the patient is undergoing VF and the defibrillation shock delivery control circuit 134 has been set to administer an enhanced energy therapeutic shock, a shock of about 40 joules may be appropriate. Because each patient must be evaluated on an individual basis, it is contemplated that the invention allows a physician to preselect a therapeutic energy value appropriate for a given type of arrhythmia for both nominal and enhanced energy shocks. It should be noted that use of the term defibrillation shock delivery control circuit 134 is not intended to mean that only defibrillation shocks are controlled, but includes control of all shocks other than pacing pulses.

The RAM 120 stores cardiac event information each time the microprocessor detect a cardiac event. Cardiac events include: (1) detection of a rate zone that is different than the current rate zone; (2) detection of other criteria for cardiac arrhythmia within the rate zone; (3) application of therapy by the defibrillation shock delivery control circuit 134; (4) application of bradycardia support pacing by a pacemaker; and (5) restoration of normal sinus rhythm ("NSR"). When any of these cardiac events occurs, the RAM 120 records the information associated with the cardiac event. The information includes the date and time of the cardiac event, the type of cardiac event occurring, the stable heart rate (if arrhythmia was detected) or the maximum heart rate (if arrhythmia was not detected). The recorded information will then form a chronology of the cardiac event episode from onset to termination.

Figure 2:
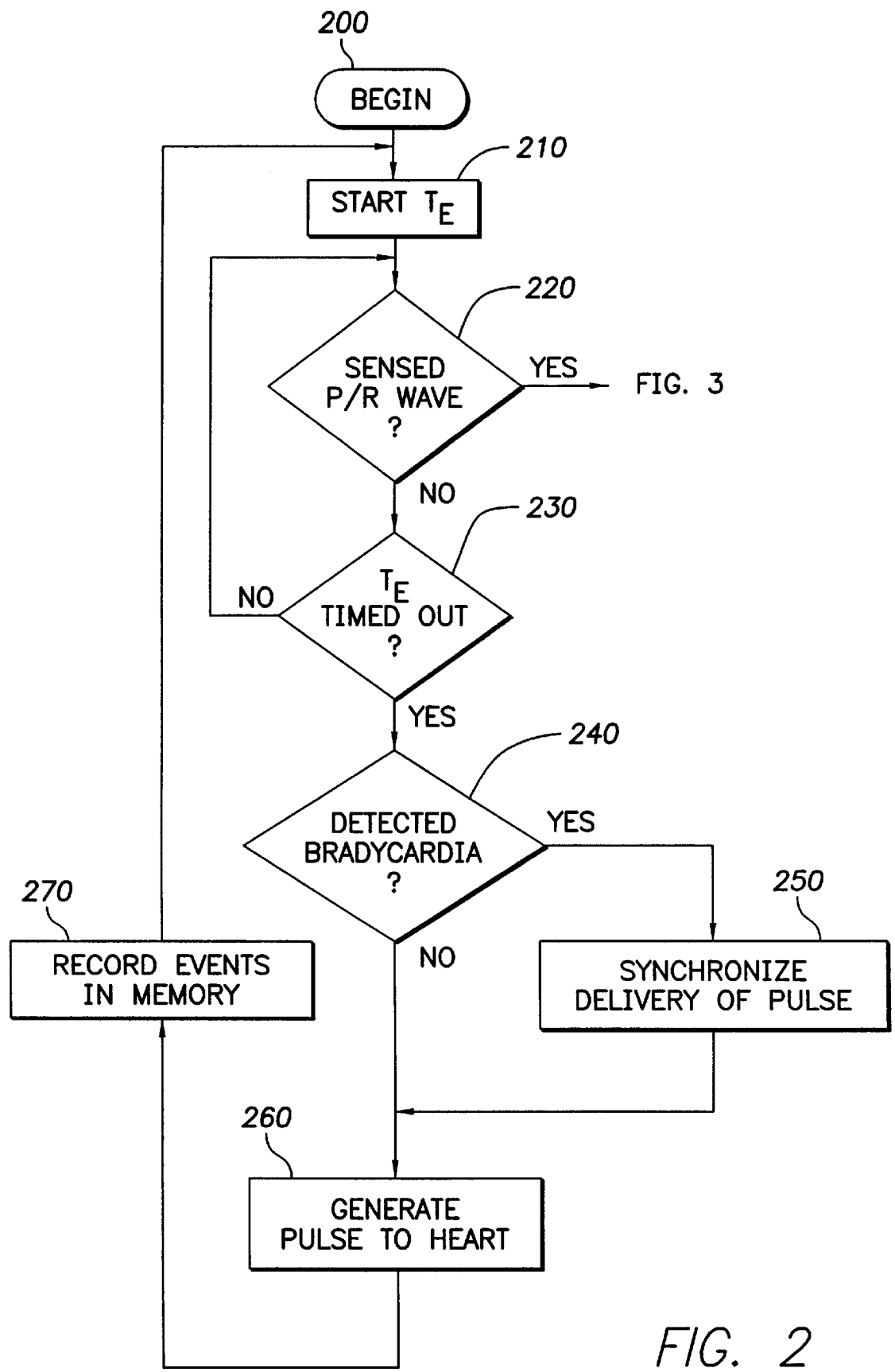
FIG. 2 is a flowchart describing the decisional steps of the method employed by the ISD of FIG. 1 to automatically record cardiac episode history in one embodiment of the invention.

FIG. 2 is a flowchart describing the decisional steps of an exemplary method used to record cardiac episode history. At step 200, the process begins by initiating a desired pacing mode. The type of pacing mode such as, for example, VVI, DDI, AVI, or DDDR, is not material for the purposes of the invention. As noted above, the microprocessor 118 determines the existence of an arrhythmia based on physiological signals received from the heart 106. Moreover, the microprocessor 118 determines, among other things, the heart rate based on an escape interval ("TE"). Typically, TE is a programmable interval determined by the physician. Once in the desired pacing mode, TE is started at step 210. Upon triggering TE, the microprocessor 118 monitors cardiac activity by determining if a P-wave (indicating contraction of the atrium) or an R-wave (indicating contraction of the ventricle) is sensed. As used in this patent document, the R-wave refers to the entire native QRS complex as seen on an electrocardiogram (ECG). At step 220, if a P/R-wave is sensed before the TE times out, then the process continues in FIG. 3 to determine whether a tachycardia is present.

On the other hand, if a P/R wave is not sensed at step 220, then at step 230, the microprocessor 118 determines if TE has timed out. If TE has not timed out, then the microprocessor 118 continues to monitor the presence of a P/R wave. If TE times out, the microprocessor 118 determines whether a bradycardia condition is present at step 240. If a bradycardia condition is detected, then at step 250, the microprocessor 118 synchronizes delivery of a pacing pulse with the P/R wave of the heart. One approach for achieving synchronization is to wait a time T1 after the R-wave before generating and transmitting a pulse signal at step 260. The time T1 is selected to be long enough to ensure that the T-wave has terminated, but also short enough to occur before the following P-wave. Typically, values of T1 about 200–300 milliseconds generally meet these criteria. These times may be adjusted to be somewhat shorter for a tachycardia condition and longer for a bradycardia condition. On the other hand, if a bradycardia condition is not present, then proceeding directly to step 260, the microprocessor 118 triggers the pacing pulse regulation and delivery circuit 136 to deliver appropriate pacing pulses to the heart 106.

After the detection of the foregoing events, at step 270, the microprocessor 118 stores the events just occurring in the heart in the memory unit 126 for later retrieval. As noted above, the events include data such as the date/time of the cardiac event, the nature of the cardiac event, the type of therapy applied by the implanted device, the number of applied therapeutic attempts, and the various heart rates during the cardiac episode. The recording of the events preferably continues until NSR is restored to the heart 106. The process repeats at step 210 by resetting and initiating a new TE.

Figure 3:
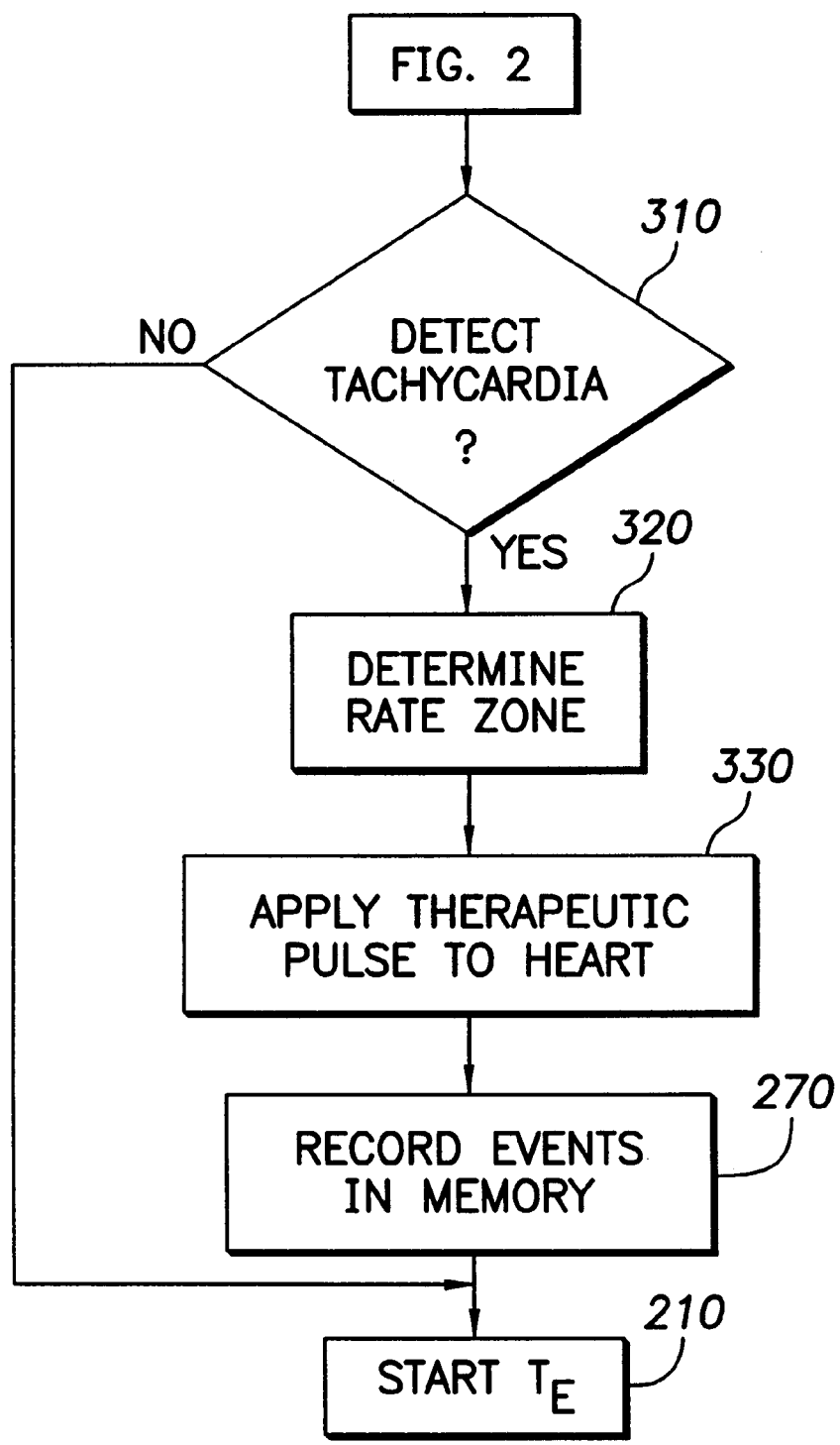
FIG. 3 is a continuation of the flowchart of FIG. 2.

As noted above, at step 220, if a P/R-wave is sensed before the TE times out, the process continues in FIG. 3 to determine whether a tachycardia is present. FIG. 3 is a continuation of the process described in FIG. 2. At step 310, the microprocessor 118 determines if a tachycardia condition is present. Typically, this determination is accomplished by examining if the P/R-wave is recurring faster than a duration T2. Determining the duration T2 may be carried out by monitoring the heart for more than one cardiac cycle, or may be based on programmable thresholds which may be entered into the ISD 100 by the physician. If a tachycardia condition is not present, then the process returns to initiate a new TE at step 210 of FIG. 2.

If a decision is made that a tachycardia condition exists, then, at step 320, the microprocessor 118 determines the rate zone to which the heart rate belongs. As noted above, there are at least five rate zones: (1) bradycardia having a heart rate of less than 60 bpm; (2) normal sinus rate ("NSR") having a heart rate between 60 and 100 bpm; (3) ventricular tachycardia 1 ("VT1") having a heart rate between 100 and 150 bpm; (4) ventricular tachycardia 2 ("VT2") having a heart rate between 150 and 230 bpm; and (5) ventricular fibrillation ("VF") having an unsynchronized heart rate greater than 230 bpm. The microprocessor 118 distinguishes among the various heart conditions, and delivers a particular type or pattern of high energy stimulation pulses specifically applicable to the detected heart condition. Pursuant to this determination, at step 330, the shock delivery circuit 144 (FIG. 1) is triggered to apply the appropriate therapeutic pulse signal to the heart 106 in an attempt to break the sensed tachycardia. The application of therapeutic pulses repeats as often as is necessary to break the tachycardia. At step 270, the microprocessor 118 stores the events just occurring in the heart 106 in the memory unit 126 for later retrieval. As noted above, the events include data such as the date/time of the cardiac event, the nature of the cardiac event, the type of therapy applied by the implanted device, the number of applied therapeutic attempts, and the various heart rates during the cardiac episode. The recording of the events preferably continues until NSR is restored to the heart 106. The process repeats at step 210 by resetting and initiating a new TE.

Figure 4:
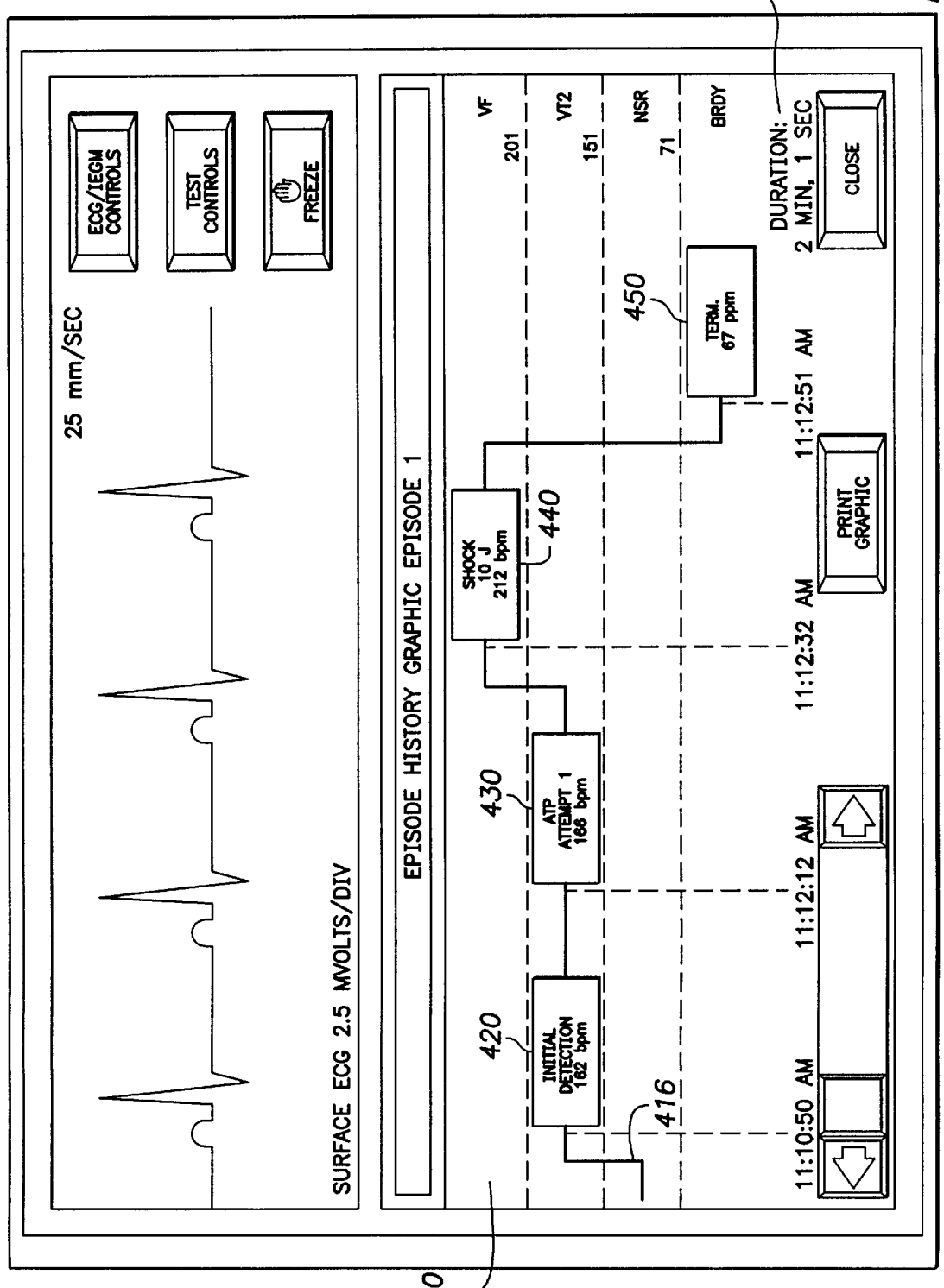
FIG. 4 is a first exemplary display of the format of presentation of the recorded episode history.

FIG. 4 is a first exemplary display of the format of presentation of the recorded episode history. Cardiac events are displayed for analysis after retrieval from the ISD 100. Data representing the cardiac events are typically stored in the memory unit 126 (FIG. 1). As shown in FIG. 4, the cardiac events are presented in a form of an episode history graph 410. In this example, prior to 11:10:50 AM, the graph 410 indicates at point 416 that the heart is in the NSR state. At time 11:10:50 AM, the recorded data of block 420 indicate that the heart has entered a VT2 state by detecting a heart rate of 162 bpm. As shown in block 430, at time 11:12:12 AM, the ISD 100 recorded a heart rate of 166 bpm and performed a first attempt of applying an antitachycardia pulse ("ATP"). As shown in block 440, at time 11:12:32 AM, the recorded data indicate that the heart entered a VF state by detecting a heart rate of 212 bpm. In response to the VF state, the ISD 100 applied a shock pulse of 10 Joules to the heart. As shown in block 450, the recorded data indicate that the cardiac episode was terminated and the heart rate was restored to 67 bpm. Finally, the duration of the cardiac episode is indicated at position 460 as 2 minutes and 1 second.

Figure 5:
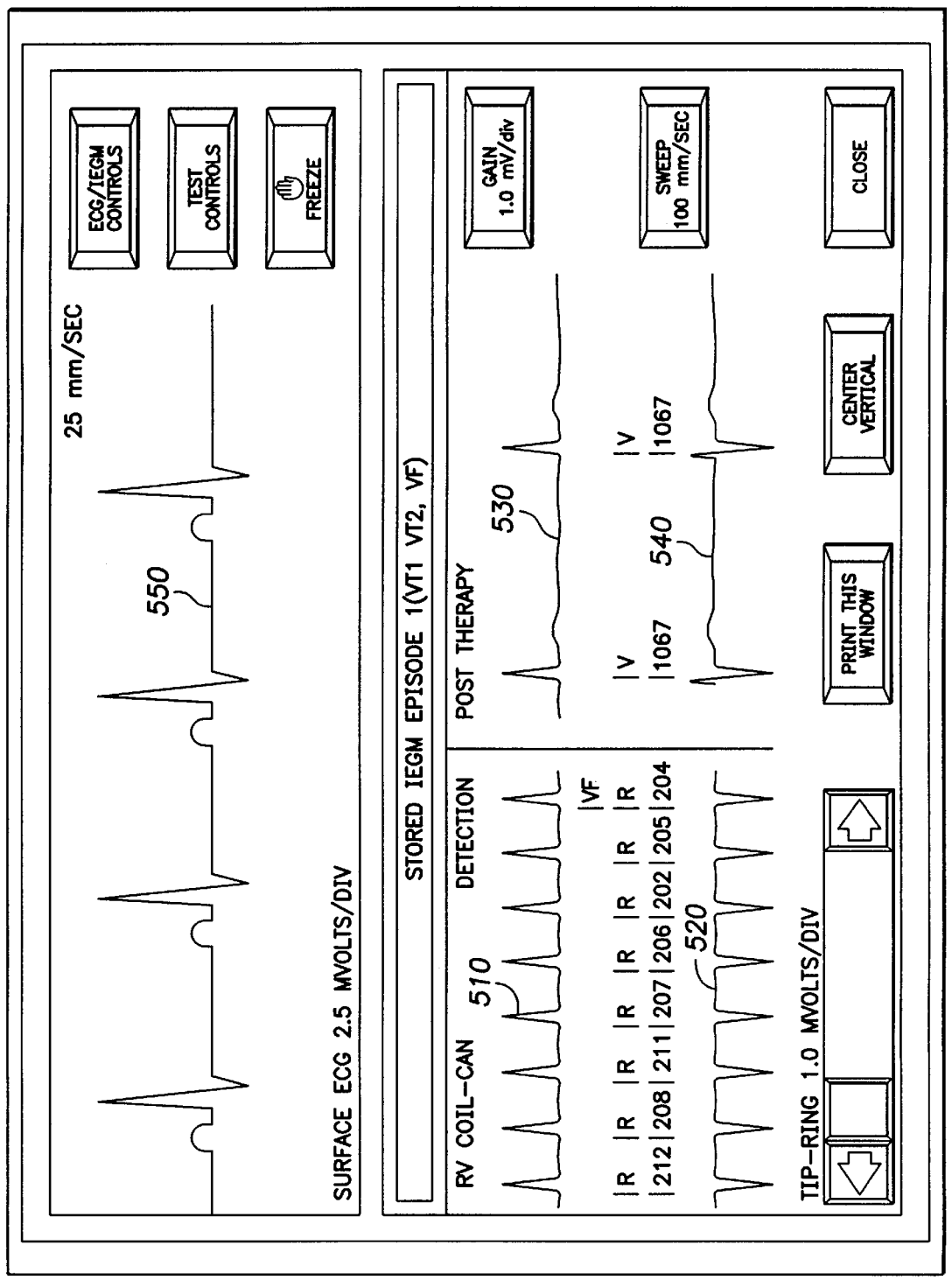
FIG. 5 is a second exemplary display of the format of presentation of the recorded episode history.

Depending on the particular therapy being applied, other information may also be recorded and displayed. FIG. 5 shows a second exemplary display of the format of presentation of the recorded episode history. In this example, the recorded data represent information in connection with the intracardiac electrogram (IEGM). The IEGM is a graphic depiction of the electrical signal emitted by active cardiac tissue. The IEGM is typically recorded through electrodes placed within the heart (e.g., using the leads 108 and/or 110 of FIG. 1). As shown in FIG. 5, in the lower-left block of the graph 500, two IEGM graphs are recorded during a cardiac episode 1. The first IEGM graph 510 is recorded using RV coil-can electrodes. The second IEGM graph 520 is recorded using tip-ring electrodes. In the lower-left block of the graph 500, various heart rates for the patient during the episode 1 are also shown as 212, 208, 211, 207, 206, 202, 205 and 204 bpm.

In the lower-right block of graph 500, IEGM graphs for the heart of the same patient after the application of therapeutic pulses are also provided. The graph 530 represents a post-therapy IEGM graph using the same RV coil-can electrodes. The graph 540 represents a post-therapy IEGM graph using the same Tip-Ring electrodes. In addition to the IEGM graphs, surface ECG may also be presented for further diagnostic efficacy. The graph 550 depicts such ECG representation as measured from the surface of the patient's body.

Figure 6:
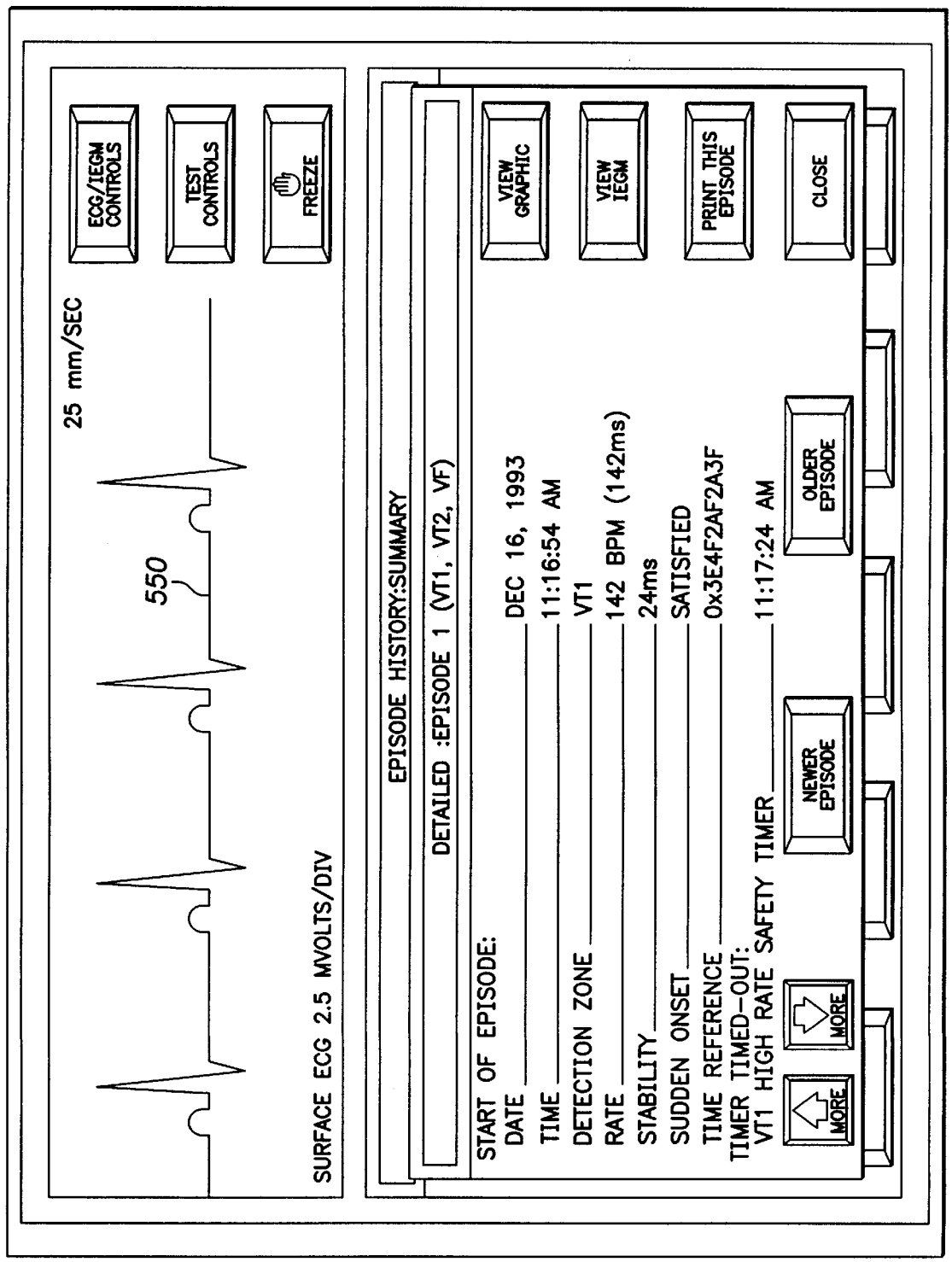
FIG. 6 is a third exemplary display of the format of presentation of the recorded episode history.

FIG. 6 is a third exemplary display of the format of presentation of the recorded episode history. In this figure, the cardiac episode is presented in a summary form. Information in the summary may include time/date of the episode, detection zone and rate of the heart, duration of stability, and whether the onset is satisfied. The foregoing presentations of the recorded data provide a powerful tool for physicians in evaluating the efficacy of the particular therapy.

In view of the foregoing, it will be appreciated that the invention overcomes the long-standing need for a system and method of recording and presenting cardiac episode history. The invention may be embodied in other specific forms without departing from its spirit or essential characteristics. The described embodiment is to be considered in all respects only as illustrative and not restrictive. The scope of the invention is, therefore, indicated by the appended claims rather than by the foregoing description. All changes, which come within the meaning and range of equivalency of the claims, are to be embraced within their scope.

What is claimed is:

1. A system, including an implantable cardiac stimulation device, for analyzing efficacy of cardiac stimulation therapy by storing and displaying historical data related to episodes of cardiac stimulation therapy, the system comprising:

sensing means for sensing a patient's cardiac rhythm which changes as a function of time;

detection means for detecting a plurality of pathological cardiac rhythms;

means for classifying each episode of a cardiac rhythm into one of a plurality of rate zones;

stimulation means for delivering cardiac stimulation therapy to a patient's heart based on the rate zone of the cardiac rhythm;

means for storing data related to each episode of cardiac stimulation therapy as a function of time, the data including information indicative of the cardiac stimulation therapy delivered, the rate zone in which the cardiac rhythm was classified and the time that the cardiac stimulation therapy was delivered; and display means, telemetrically coupled to the storing means, for graphically displaying the data along an x-axis and a y-axis as a function of the time that the cardiac stimulation therapy was delivered;

whereby the plurality of rate zones are displayed along the y axis and the time that each episode of cardiac stimulation therapy was delivered is displayed along the x axis.

2. The system for displaying the historical data, as recited in claim 1, wherein the stimulation means comprises means for providing at least one of bradycardia, rate-responsive, antitachycardia, cardioversion, and defibrillation stimulation therapy.

3. The system for displaying historical data, as recited in claim 1, further comprising:

means for triggering the storing means to store the data whenever a new cardiac stimulation therapy is applied.

4. The system for displaying historical data, as recited in claim 1, further comprising:

means for triggering the storing means to store the data whenever the cardiac rhythm has been detected in a new rate zone.

5. The system for displaying historical data, as recited in claim 1, wherein the detection means includes means for detecting the cardiac rhythm based on a plurality of detection criteria, further comprising:

means for triggering the storing means to store the data whenever a new detection criteria is needed to detect the cardiac rhythm.

6. The system for displaying historical data, as recited in claim 1, further comprising:

means for triggering the storing means to store the data whenever bradycardia support therapy is applied.

7. The system for displaying historical data, as recited in claim 1, further comprising:

means for triggering the storing means to store the data whenever a normal sinus rhythm has been restored.

8. The system for displaying historical data, as recited in claim 1, further comprising:

the storing means includes means for storing a date and time of the episode of cardiac stimulation therapy.

9. The system for displaying historical data, as recited in claim 1, further comprising:

the storing means includes means for storing a number of attempts associated with applying the cardiac stimulation therapy.

10. The system for displaying historical data, as recited in claim 1, further comprising:

the storing means includes means for storing a patient's heart rate between each episode of cardiac stimulation therapy.

11. The system for displaying historical data, as recited in claim 1, further comprising:

means for displaying the patient's heart rate as a function of time; and means for annotating the display of the patient's heart rate with the data related to each episode of cardiac stimulation therapy.

12. The system for displaying historical data, as recited in claim 1, further comprising:

means for sensing a physiological historical parameter of the patient corresponding to exercise level;

means for determining a sensor-indicated rate based on the sensing means; and wherein the storing means includes means for storing the sensor-indicated rate. of a plurality of zones;

applying a cardiac stimulation therapy to the patient's heart in response to the detected pathological cardiac rhythm;

recording data related to the pathological cardiac rhythm and stimulation therapy; and displaying the data for analysis.

13. A system, including an implantable cardiac stimulation device, for analyzing historical data related to applications of cardiac stimulation therapy, the system comprising:

detection means for detecting a plurality of cardiac rhythms;

means for classifying each of the cardiac rhythms into a one of a plurality of pre-defined rate zones based upon the rate of such cardiac rhythm;

stimulation means for delivering at least one type of cardiac stimulation therapy to a patient's heart based upon the rate zone of the cardiac rhythm;

means for storing data related to the cardiac stimulation therapy for each episode of cardiac rhythm as a function of time, the data including information indicative of the cardiac stimulation therapy delivered, the rate zone in which the cardiac rhythm was classified and the time that the cardiac stimulation therapy was delivered; and display means for graphically displaying the data along an x-axis and a y-axis as a function of the time that the cardiac stimulation therapy was delivered;

whereby the plurality of rate zones are displayed along the y-axis and the time that each episode of cardiac stimulation therapy was delivered is displayed along the x-axis.

14. In an implantable cardiac stimulation device, a method of analyzing efficacy of cardiac stimulation therapy, the method comprising the steps of:

sensing a patient's cardiac rhythm as a function of time;

detecting a pathological cardiac rhythm upon occurrence;

classifying the pathological rhythm into one of a plurality of zones;

delivering a cardiac stimulation therapy to the patient's heart in response to the detected pathological cardiac rhythm;

recording data related to the pathological cardiac rhythm, the stimulation therapy and the time that the stimulation therapy was delivered; and displaying the data for analysis along an x-axis and a y-axis as a function of the time that the cardiac stimulation therapy was delivered;

whereby the plurality of rate zones are displayed along the y-axis and the time that each episode of cardiac stimulation therapy was delivered is displayed along the x-axis.

15. The method as defined in claim 14, wherein the step of recording data includes the step of recording the heart rate and the type of cardiac stimulation therapy.

16. The method as defined in claim 14, wherein the step of displaying the data includes the step of displaying the heart rate and the type of cardiac stimulation therapy as a function of time.

17. The method as defined in claim 14, wherein the step of delivering cardiac stimulation therapy includes the step of delivering at least one of a bradycardia, rate-responsive, antitachycardia, cardioversion, and defibrillation therapy.

18. The method as defined in claim 14, further comprising the step of initiating storage of the data whenever a new cardiac stimulation therapy is applied.

19. The method as defined in claim 14, further comprising the step of initiating storage of the data whenever the cardiac rhythm is detected in a different zone.

20. The method as defined in claim 14, further comprising the step of initiating storage of the data whenever a new detection criteria is needed to detect the cardiac rhythm.

21. A system for analyzing efficacy of cardiac stimulation during a cardiac episode, the system comprising:

a first circuit which senses a patient's cardiac rhythm as a function of time;

a detector which detects a pathological cardiac rhythm upon occurrence;

a processor which classifies the pathological cardiac rhythm into one of a plurality of zones;

a second circuit which delivers a cardiac stimulation therapy to the patient's heart in response to the pathological cardiac rhythm;

a memory which stores data related to the pathological cardiac rhythm, the stimulation therapy and the time that the stimulation therapy was delivered; and a display unit, telemetrically coupled to the memory, which displays the data for analysis along an x-axis and a y-axis as a function of the time that the cardiac stimulation therapy was delivered;

whereby the plurality of rate zones are displayed along the y-axis and the time that each episode of cardiac stimulation therapy was delivered is displayed along the x-axis.

22. The system as defined in claim 21, wherein the second circuit delivers at least one of bradycardia, rate-responsive, antitachycardia, cardioversion, and defibrillation stimulation therapy.

23. The system as defined in claim 21, wherein the processor is programmed to trigger the memory to store data whenever a cardiac stimulation therapy is applied.

24. The system as defined in claim 21, wherein the processor is programmed to trigger the memory to store data whenever the cardiac rhythm is detected in a different rate zone.

25. The system as defined in claim 21, wherein the detector detects the cardiac rhythm based on a plurality of detection criteria, and the processor triggers the memory to store data whenever a different detection criteria is needed to detect the cardiac rhythm.

26. The system as defined in claim 21, wherein the memory stores the date and time of the cardiac episode.

27. The system as defined in claim 21, wherein the memory stores the number of attempts associated with the cardiac stimulation therapy.

* * * * *